United States Patent [19]

Herrington et al.

[11] 4,323,508

[45] Apr. 6, 1982

[54] PROCESS FOR THE MANUFACTURE OF FURAN COMPOUNDS

[75] Inventors: Daniel R. Herrington, Chesterland; Albert P. Schwerko, Solon, both of Ohio

[73] Assignee: The Standard Oil Company, Cleveland, Ohio

[21] Appl. No.: 8,716

[22] Filed: Feb. 2, 1979

Related U.S. Application Data

[63] Continuation of Ser. No. 866,313, Jan. 3, 1978, abandoned.

[51] Int. Cl.$^3$ .............................................. C07D 307/36
[52] U.S. Cl. .................................................. 260/346.11
[58] Field of Search .................................... 260/346.11

[56] References Cited

U.S. PATENT DOCUMENTS

| | | | |
|---|---|---|---|
| 2,900,396 | 8/1959 | Harrison | 260/346.11 |
| 3,238,225 | 3/1966 | Brill et al. | 260/346.11 |
| 3,894,055 | 7/1975 | Farka et al. | 260/346.11 |
| 3,933,861 | 1/1976 | Kurkov | 260/346.11 |

FOREIGN PATENT DOCUMENTS 52-77049 6/1977 Japan.

*Primary Examiner*—Richard Raymond
*Attorney, Agent, or Firm*—Gary R. Plotecher; Herbert D. Knudsen; Larry W. Evans

[57] ABSTRACT

The present invention relates to a process for the manufacture of furan compounds by the direct oxidation of conjugated diolefins with air or oxygen in the liquid phase in the presence of a transition metal catalyst system.

31 Claims, No Drawings

PROCESS FOR THE MANUFACTURE OF FURAN COMPOUNDS

This is a continuation of application Ser. No. 866,313 filed Jan. 3, 1978, now abandoned.

BACKGROUND OF THE INVENTION

Present processes for the direct oxidation of diolefins to furan compounds are primarily vapor phase processes which are generally characterized by low conversions and poor selectivities. These disadvantages are brought about by the instability of furan compounds at high temperatures in the presence of oxygen which leads to the formation of resinous compounds, charring and uncontrolled polymerization. The liquid phase process of the present invention eliminates these disadvantages by operating at moderate temperatures.

Although several liquid phase processes are known for the production of furan compounds, they involve the use of oxygenated compounds as starting materials. For example, U.S. Pat. No. 3,932,468, issued Jan. 13, 1976, and U.S. Pat. No. 3,996,248, issued Dec. 7, 1976, pertain to the rearrangement of butadiene monoxide, and U.S. Pat. No. 3,933,861, issued Jan. 20, 1976, involves the reaction of an alkene and an alkene oxide to yield substituted furans. Both of these processes require oxygenated starting materials, whereas in the present invention, furan compounds are obtained by the direct oxidation of the conjugated diolefin.

While Japanese Pat. No. 77 77,049 discloses a process for the oxidation of butadiene to furan in an aqueous acidic medium, the process of the present invention is distinguished from this process in that the present process is conducted in an organic solvent medium in which the catalyst and furan products are more stable.

SUMMARY OF THE INVENTION

In accordance with the process of the present invention, acyclic conjugated diolefins containing from 4 to 10 carbon atoms are converted to furan and alkyl-substituted furan compounds by the direct oxidation of the diolefin with molecular oxygen in a liquid phase reaction. The reaction is carried out in a non-aqueous reaction medium in the presence of a transition metal organo-metallic catalyst complex.

The liquid phase oxidation reaction of this invention is a free radical reaction, and these reactions appear to be initiated by means of the formation of an initial free radical. This initial free radical may generate the desired product (furan) directly, or proceed to form other radical intermediates which can yield either furan, other oxygenated products, such as a diolefin monoxide, 2,5-dihydrofuran, crotonaldehyde, or oligomers and/or polymers.

The role of the catalyst of this invention is to react with the initial key radical intermediates, converting them directly to furan products before deleterious by-products can be produced. It is this selective catalytic behavior, coupled with specific reaction conditions herein defined that result in the enhanced selectivity of the oxidation of the diolefins to the desired furan compounds.

Suitable feeds in this invention for conversion to furan compounds comprise acyclic alkadienes having from 4 to 10 carbon atoms. Examples include butadiene-1,3 pentadiene-1,3, isoprene, hexadiene-1,3, decadiene-1,3, and the like, and mixtures thereof. The acyclic alkadienes having from 4 to 5 carbon atoms are preferred in this process. The furan compounds produced by the process of the present invention have the formula:

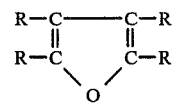

wherein each R is individually selected from the group consisting of hydrogen and an alkyl radical having from 1 to 6 carbon atoms, the total carbon atoms in the R radicals being in the range of 0 to 6. Representative products include furan, 2-methylfuran, 3-methylfuran, 2,5-diethylfuran, 2-n-hexylfuran, 2-isopropyl-3-methylfuran, 3,4-dipropylfuran, 3-methyl-4-n-butylfuran, and the like.

The catalysts of this invention are organo-metallic complexes or salts of the metals of Groups IVB, VB, VIB, VIIB or VIII of the Periodic classification of elements. These complexes have the general formula:

$$[R_x M (L)_y]_z$$

wherein
R is an organic ligand selected from the group consisting of alkyl, aryl, alkene, diene, triene or alkyne radicals containing from 1 to 8 carbon atoms;
L is a ligand selected from the group consisting of carbon monoxide and a halogen;
M is a transition metal or their mixtures selected from the groups IVB, VB, VIB, VIIB and VIII of the Periodic classification of elements;
and wherein
x is 0 to 2,
y is 0 to 6, and
x+y is 1 to 6,
and wherein z is 1 to 6.

Specific examples of suitable catalysts include $OsCl_3$, $Os_3(CO)_{12}$, $[CpMo(CO)_3]_2$ (Cp=cyclopentadienyl radical), $CpV(CO)_4$, $CpTiCl_2$, $CpMn(CO)_3$, $(Cp)_2Fe$, $Mo(CO)_6$, $[CpFe (CO)_2]_2$, $(C_4H_6)Fe(CO)_3$, $Co_2(CO)_8$, $Ru_3(CO)_{12}$, $Rh_6(CO)_{16}$ and $W(CO)_6$.

While these complexes and salts are effective catalysts in their own right, it may also be advantageous to utilize certain promoters for these catalysts as defined by the general formula:

$$A R_m X_n$$

wherein
A can be mercury, thallium, indium, or a Group IV A element such as silicon, germanium, tin or lead;
R can be a hydride, alkyl, aryl or an amine group;
X can be an anion of a mineral acid or a carboxylic acid,
and wherein
m is 0–4,
n is 0–4, and
m+n is 1 to 4.

Specific examples of these types of promoters include such compounds as $Hg(C_2H_3O_2)_2$, $SnCl_2$, $(C_2H_5)_2SnCl_2$, $SnCl_4$, $(CH_3)_3SnN(CH_3)_2$, $GeI_2$, $(n-C_4H_9)_3GeI$, $(\gamma-C_5H_5)Ge(CH_3)_3$, $(C_2H_5)_3 PbCl$, $(CH_3)_3 SiH$, or $SiH_3I$.

When promoters are employed for the catalysts of this invention, they may be added to the reaction mixture as separate species or they may be reacted with the catalyst to give a separate chemical compound which can be isolated and purified prior to its use as a catalytic agent. Representative examples of compounds formed by reactions occurring between the catalyst and the promoter include: $ClHgFe(Cp)_2$, $Hg[Co(CO)_4]_2$, $Cl_2Sn[Fe(CO)_2Cp]_2$, $I_2Ge[Co(CO)_4]_2$, $[(C_2H_5)_3Pb]_2Fe(CO)_4$, $H_3SiCo(CO)_4$, $Cl(CH_3)_2Sn[Mn(CO)_5]$, and $[Cp(CO)_3Mo-Sn(CH_3)_2-Mn(CO)_5]$.

The promoter compounds of the catalyst system are advantageously employed in molar ratios of from 0.25 to 2.0 moles of promoter per mole of the transition metal catalyst. However preferred molar ratios of promoter compound to the transition metal catalyst are about 0.5:1 to 2:1. The catalysts of this invention (with or without promoters) may be dissolved in the reaction medium as homogeneous catalysts, slurried in the reaction medium as insoluble, unsupported heterogeneous catalysts, or in some cases where advantageous, they may be supported on carriers such as silica, alumina, or polymeric materials and slurried in the reaction medium. It is preferred, however that the catalyst system be a homogeneous system where the catalyst is soluble in the reaction solvent. The concentration of the catalyst in the solvent medium may range from $10^{-6}$ to 10.0 moles/liter. Preferably a catalyst concentration of from about $10^{-5}$ to 1.0 moles/liter is employed.

The reaction medium suitable for the process of this invention is an essentially inert, non-coordinating or weakly coordinating organic solvent having a boiling point significantly higher than the boiling points of the feed or the products obtained. Solvents with boiling points of from 130° to 225° C. are especially preferred. Also desirable are those solvents having an absence of abstractable hydrogens which could lead to oxidation of the solvent or the binding of the active sites of the metal or metals in the catalyst, thereby deactivating the catalyst. Examples of suitable solvents include paraffinic hydrocarbons, aromatic hydrocarbons, chlorinated hydrocarbons, and nitrile aromatics such as heptanes, decanes, and the like; toluene and the xylenes; chlorobenzene, chloroform, carbon tetrachloride, etc.; and benzonitrile; with chlorobenzene being the most preferred. Substituted furans such as alkyl-furans or 2,3-benzofuran may also serve as suitable solvents in some cases.

The oxidation reaction of the present invention is very sensitive to reaction conditions and it is an essential feature of the invention that the reaction be carried out under conditions which maximize selectivity. The reaction may be carried out at temperatures in the range of from about 20° to 200° C., and preferably at temperatures in the range of from about 50° to 130° C. Temperatures above this range bring about the formation of additional oxidation products such as crotonaldehyde and increase the formation of undesirable polymer.

The reaction pressure may range from 1 to 20 atmospheres, and preferably from 1 to 10 atmospheres. The partial pressure of oxygen is of particular importance to the selectivity of the reaction, and oxygen pressures of from 0.5 to 5 atmospheres and especially oxygen pressures of from 1 to 3 atmospheres are advantageously employed.

Another critical reaction variable affecting selectivity of the reaction is the ratio of diolefin to oxygen. While the molar ratio of diolefin to oxygen may vary from 0.001 to 100.0, a ratio of from 0.33 to 5.0 is preferred.

In those instances where the reaction is carried out in a sealed reaction vessel, the reaction times may range from 0.5 to 10 hours and a reaction time of from 1.0 to 4 hours is preferable. Continuous operation in which the reaction mixture is maintained at constant temperature and pressure is also contemplated to be within the scope of the present invention. Under such conditions, the diolefin and air or oxygen are continuously fed to the reactor while volatile products and the unreacted feed are continuously removed. The volatile products can be collected and the unreacted feed recycled to the reactor.

The reactor vessel may be constructed from stainless steel, or in certain instances the reaction vessel may be lined with glass, quartz or a stable resinous material in order to minimize side reactions between reaction intermediates and the walls of the reaction vessel.

SPECIFIC EXAMPLES

Examples 1–12

The oxidation of butadiene to furan in the presence of a variety of promoted and unpromoted transition metal catalyst complexes was conducted in a series of experiments according to the following procedure:

An amount of catalyst required to give a concentration of $1 \times 10^{-4}$ moles of catalyst in the reaction solvent was weighed into a stainless steel reaction tube (180 mm long × 9.5 mm diameter) equipped with a stainless steel ball valve and septum cap. The tube was evacuated and charged with a mixture of butadiene and oxygen in a 1:1 molar ratio at an initial oxygen pressure of 2.2 atmospheres. Four milliliters of chlorobenzene solvent was introduced into the tube with a metering pump. The tube and its contents were heated to a temperature of 110° C. in a heating block for a period of two hours. At the end of this time period, the tube was quickly cooled to room temperature and the reaction mixture analyzed by gas chromatography.

The percent conversion of the butadiene and the percent selectivity to furan based on the percent of butadiene converted that were obtained in Examples 1 to 12 are summarized in Table I below.

TABLE I

| Example | Catalyst | % Total Conversion | % Selectivity to Furan |
|---|---|---|---|
| 1 | $(Cp)_2Fe$ | 2.9 | 99.0 |
| 2 | $(Cp)_2Fe/SnCl_2$ | 10.2 | 81.1 |
| 3 | $Mo(CO)_6$ | 1.4 | 97.7 |
| 4 | $Mo(CO)_6/Hg(C_2H_3O_2)_2$ | 16.7 | 65.4 |
| 5 | $CpV(CO)_4$ | 9.4 | 82.2 |
| 6 | $CpTi_2Cl_2$ | 13.3 | 77.5 |
| 7 | $[CpMo(CO)_3]_2$ | 17.6 | 68.2 |
| 8 | $Os_3(CO)_{12}$* | 18.2 | 92.0 |
| 9 | $Os_3(CO)_{12}/SnCl_2$ | 14.2 | 71.6 |
| 10 | $OsCl_3$ | 20.5 | 57.4 |
| 11 | $Ru_3(CO)_{12}$ | 0.1 | 100.0 |
| 12 | $Ru_3(CO)_{12}/(n-C_4H_9)_3GeI$ | 13.2 | 99.0 |

(Cp = cyclopentadiene)
*Reaction conducted in a resin coated stainless steel reactor.

We claim:

1. A process for converting acyclic conjugated diolefinic hydrocarbons containing from 4 to 10 carbon atoms to furan and alkyl-substituted furans comprising reacting said conjugated diolefins with molecular oxygen in the liquid phase in an inert organic solvent in the presence of a catalyst having the composition:

$$[R_xM(L)_y]_z$$

wherein
- R is an organic ligand selected from the group consisting of alkyl, aryl, alkene, diene, triene, or alkyne radicals containing from 1 to 8 carbon atoms;
- L is a ligand selected from the group consisting of carbon monoxide and a halogen;
- M is a transition metal or mixtures thereof, selected from Groups IVB, VB, VIB, VIIB and VIII of the Periodic classification of elements;

and wherein
- x is 0 to 2,
- y is 0 to 6, and
- x+y is 1 to 6, and wherein z is 1 to 6.

2. The process in claim 1 wherein the catalyst is promoted with a compound having the formula:

$$A\ R_m\ X_n$$

wherein
- A is an element selected from the group consisting of mercury, thallium, indium, silicon, germanium, tin and lead;
- R is a hydride, an alkyl, aryl or an amine radical; and
- X is an anion of a mineral acid or a carboxylic acid;

and wherein
- m and n each are numbers from 0 to 4, and
- m+n is 1 to 4.

3. The process in claim 2 wherein the promoter is employed in a molar ratio of from 0.25 to 2.0 moles per mole of the transition metal catalyst.

4. The process in claim 3 wherein the reaction is carried out within the temperature range of 20° to 200° C.

5. The process in claim 4 wherein the molar ratio of diolefin to oxygen is within the range of 0.001 to 100.0.

6. The process in claim 5 wherein the reaction is carried out in an inert organic solvent having a boiling point in the range of from 130° to 225° C.

7. The process in claim 6 wherein the solvent is selected from the group consisting of paraffinic hydrocarbons, aromatic hydrocarbons, chlorinated hydrocarbons, nitrile aromatics, and alkyl or aryl-substituted furans.

8. The process in claim 7 wherein the solvent is chlorobenzene.

9. The process in claim 6 wherein the catalyst is soluble in the reaction solvent.

10. The process in claim 6 wherein the catalyst is slurried in the reaction solvent.

11. The process in claim 5 wherein the diolefin is butadiene.

12. The process of claim 1 wherein said acyclic conjugated diolefinic hydrocarbon is at least one of butadiene, pentadiene, isoprene, hexadiene and decadiene.

13. The process of claim 1 wherein said catalyst is selected from the group consisting of $OsCl_3$, $Os_3(CO)_{12}$, $[CpMo(CO)_3]_2$ (Cp=cyclopentadienyl radical), $CpV(CO)_4$, $CpTiCl_2$, $CpMn(CO)_3$, $(Cp)_2Fe$, $Mo(CO)_6$, $[CpFe(CO)_2]_2(C_4H_6)$ $Fe(CO)_3$, $Co_2(CO)_8$, $Ru_3(CO)_{12}$, $Rh_6(CO)_{16}$ and $W(CO)_6$.

14. The process of claim 2 wherein said catalyst contains a promoter selected from the group consisting of $Hg(C_2H_3O_2)_2$, $SnCl_2$, $(C_2H_5)_2SnCl_2$, $SnCl_4$, $(CH_3)SnN(CH_3)_2$, $GeI_2$, $(n-C_4H_9)_3GeI$, $(\gamma-C_5H_5)Ge(CH_3)_3$, $(C_2H_5)_3PbCl$, $(CH_3)_3SiH$, or $SiH_3I$.

15. The process of claim 2 wherein said catalyst is selected from the group consisting of $ClHgFe(Cp)_2$, $Hg[Co(CO)_4]_2$, $Cl_2Sn[Fe(CO)_2Cp]_2$, $I_2Ge[Co(CO)_4]_2$, $[(C_2H_5)_3Pb]_2Fe(CO)_4$, $H_3SiCo(CO)_4$, $Cl(CH_3)_2Sn[Mn(CO)_5]$, and $[Cp(CO)_3Mo-Sn(CH_3)_2-Mn(CO)_5]$.

16. The process of claim 1 wherein X is a positive number and Y is zero.

17. The process of claim 16 wherein X is 2 and M is Fe.

18. The process of claim 1 wherein Y is a positive number and X is zero.

19. The process of claim 18 wherein M is Os.

20. The process of claim 1 wherein X and Y are both positive numbers.

21. The process of claim 20 wherein X is 2, Y is 2 and M is Ti.

22. The process of claim 1 wherein M is at least one element selected from the group consisting of Group IVB, Group VB, Group VIB, Group VIIB, Os, Fe, Ru, Co, Rh and Ir.

23. The process of claim 22 wherein M is selected from Fe, Os, Mo, Ti, V and Ru.

24. The process of claim 23 wherein M is selected from Fe and Os.

25. The process of claim 1 wherein R is cyclopentadienyl.

26. The process of claim 1 wherein L is CO.

27. The process of claim 1 wherein L is Cl.

28. The process of claim 2 wherein A is selected from the group consisting of Ge and Sn.

29. The process of claim 2 wherein A is Sn and M is Fe.

30. The process of claim 2 wherein A is Ge and M is Ru.

31. The process of claim 1 wherein said process is conducted in the absence of substantial amounts of water.

* * * * *